United States Patent [19]

Tesi

[11] Patent Number: 4,569,673
[45] Date of Patent: Feb. 11, 1986

[54] BACTERIAL BARRIER FOR INDWELLING CATHETERS AND OTHER MEDICAL DEVICES

[75] Inventor: Julius M. Tesi, Buckeye Lake, Ohio

[73] Assignee: Battelle Development Corporation, Columbus, Ohio

[21] Appl. No.: 570,125

[22] Filed: Jan. 12, 1984

[51] Int. Cl.$^4$ .............................................. A61N 1/30
[52] U.S. Cl. .......................................... 604/20; 604/8; 604/265
[58] Field of Search ................. 604/20, 21, 8, 265, 604/266

[56] References Cited

U.S. PATENT DOCUMENTS

| 486,902 | 11/1892 | Shults | 604/20 |
|---|---|---|---|
| 2,276,623 | 3/1942 | Meiman | 433/32 |
| 2,355,231 | 8/1944 | Moore | 604/20 |
| 3,848,603 | 11/1974 | Throner | 128/349 R |
| 3,964,477 | 6/1976 | Ellis et al. | 128/172.1 |
| 3,970,530 | 7/1976 | Maslowski et al. | 426/237 |
| 4,027,393 | 6/1977 | Ellis et al. | 604/20 X |
| 4,054,139 | 10/1977 | Crossley | 604/265 |
| 4,292,968 | 10/1981 | Ellis | 604/20 |
| 4,419,091 | 12/1983 | Behl et al. | 604/20 |
| 4,483,688 | 11/1984 | Akiyama | 604/265 |

FOREIGN PATENT DOCUMENTS 1106718 8/1981 Japan .................................. 604/265

Primary Examiner—John Doll
Assistant Examiner—Glenn A. Caldarola
Attorney, Agent, or Firm—Benjamin Mieliulis

[57] ABSTRACT

A novel bacterial barrier for medical devices is disclosed comprising a strip or band of oligodynamic metal connected to another conductor generally connected in open circuit to a power cell and producing a strategic circumferential zone of bacterial inhibition when the medical device is installed.

15 Claims, 3 Drawing Figures

BACTERIAL BARRIER FOR INDWELLING CATHETERS AND OTHER MEDICAL DEVICES

BACKGROUND OF THE INVENTION

1. Field of the Invention

This present invention relates to novel bacterial barrier devices. More specifically this invention relates to improved and clinically acceptable intraluminal catheters and vascular surgical shunts. The present invention discloses a bacterial barrier device which placed circumferentially around an intraluminal catheter (or surgical shunt) and positioned as just within the urethral orifice releases oligodynamic silver ions in a narrow circumferential band thus serving as a barrier to entry of bacterial infection and reducing the incidence of nosocomial problems.

2. Description of the Prior Art

Silver has long been known as an oligodynamic metal. Goodman and Gilson (1943) attributed the antibacterial properties of silver to silver ions which precipitate the protein of bacterial protoplasm. The precipitated protein continues to slowly liberate small amounts of silver ions thus sustaining an antiseptic action. Silver nitrate is routinely instilled in infants' eyes for the prophylaxis of ophthalmia neonatorum. Sollmann (1943) described the action of silver nitrate as occuring in two stages, first, an immediate germicidal effect by the direct application of silver ions and later an antiseptic effect produced by re-ionization of silver protein compounds.

Fromberg and Heiss (1937) using agar plates infected with *M. pyogenes var. aureus*, confirmed the inactivity of clean, pure silver wire but demonstrated that such a wire could be activated by coating one end with silver chloride producing a zone of inhibition. I. B. Romans, *Antiseptics, Disinfectants, Fungicides and Chemical and Physical Sterilization*, "Silver Compounds", 2nd Ed., G. Reddish editor, Philadelphia, Lea & Febiger (1957).

U.S. Pat. No. 2,121,875 Kruse (1938) describes a process for anodically coating surgical instruments and silver plates with oligodynamic silver chloride by passing current through such article while immersed in a dilute sodium chloride solution. Articles coated according to Kruse's process needed to be periodically reactivated or recoated.

Ellis in U.S. Pat. No. 4,027,393 (1977) reported that laboratory tests with *Pseudononas Aeruginosa, Proteris vulgaris, Staphyloccus aureus* and *Escherichia coli*, bacteria normally found in wounds, have verified that silver electrodes have a bacterial effect at currents of one tenth the magnitude necessary when other electrode elements are used. Ellis while principally directed to dental sterilization recognized the long standing problem of bacterial infection with catheters. Ellis proposed the sterilization of indwelling catheters using silver particles dispersed in the elastomeric catheter wall. The negative electrode is attached to the patient's body or in the effluent. Ellis also proposed to make the silver anode an intraluminal electrode with the silver anode designed as a bladder insert attached to the tip of a wire lead which extended ahead of the catheter.

Neither of the Ellis catheters gained clinical acceptance. Both the intraluminal electrode catheter and the catheter with particles of silver dispersed throughout the length of the elastomeric catheter suffer from serious clinical deficiencies. In the case of the catheter with silver particles dispersed in the elastomeric catheter, only those silver particles lying in the outer surface would release silver ions from the catheter/urethral wall interface; however, the portion of the catheter that contains silver particles must be heavily loaded to insure electrical continuity. This is not only wasteful of silver but also the elastomeric properties of the catheter in the loaded region are significantly reduced resulting in loss of flexibility with attendant difficult and added painful insertion, and continued patient discomfort while indwelling.

More seriously, in the case of the silver particle embedded catheter, the silver containing region extends well into the urethra and is contact with a large extent of mucosal lining and glands. Current flow has the physiological effect on the urethral mucosa and its many mucous secreting glands of enhancing stimulation of fluid flow. In the supine patient, the gradient of excess fluid flow would be toward the bladder rather than to the exterior, tending to wash silver ions into the bladder. This dilutes the barrier effect and the desirability of continuous transfer of silver ions into the bladder is questionable. If the current applied throughout the catheter wall exceeds the sensory threshold an uncomfortable tingling sensation can also be felt.

The Ellis intraluminal electrode catheter with the silver anode attached on a wire lead ahead of the catheter and having the silver anode inserted directly into the bladder enhances the negative aspects of silver ion presence in the bladder. Silver ions produced in the urine can alter physiological conditions causing precipitation of salts and proteins. Also, an electrode inserted into and dwelling for an extended period in the bladder could become detached thus necessitating serious retrieval efforts and surgical procedures; likewise the wire lead ahead of the catheter could puncture tissue walls leading to serious complications. Further, the intraluminal route is not considered the major pathway for infection, which instead is believed to enter through the catheter/urethral wall interface. The catheter having the silver anode inserted directly into the bladder, has the additional drawback that little, if any, silver ion can reach the catheter/urethral wall interface and bactericidal action must take place within the bladder volume.

SUMMARY OF THE INVENTION

It is an object of the present invention to provide an improved bacterial barrier for indwelling luminal and intraluminal catheters, and luminal and vascular devices.

It is another object of this invention to provide a bacterial barrier in the form of a fixed or detachable plastic band or tape having a continuous strip of silver, a more noble metal and a self contained current source.

It is another object of this invention to provide an improved catheter or vascular device or surgical shunt having a circumferential bacterial barrier position so as to be just within the external body opening at the catheter/urethral wall interface, or vascular device/vascular wall interface, in the form of a continuous strip or band of silver, a more noble metal, and a self contained current source.

DETAILED DESCRIPTION OF THE INVENTION

The present invention is that of an improved intraluminal catheter, a vascular device such as an intravenal shunt or IV-unit, or an intraluminal device having a novel bacterial barrier positioned as just within the body opening to the external environment.

The novel bacterial barrier is in the form of a fixed or detachable thin band, stretchable or shrinkable ring, or plastic nonconductive tape having a continuous strip of oligodynamic metal, such as silver, zinc, copper or aluminum, a more noble metal and a self contained current source.

The strip of oligodynamic metal and strip of more noble metal are preferably placed parallel to one another such that when the tape is applied to a catheter or intravenal shunt or other intraluminal device, the strips form essentially a continuous ring. The oligodynamic and more noble metal are connected to different poles of a self contained current source, i.e., a battery. The strip of oligodynamic metal is connected to the pole being oxidized (positive) such that the oligodynamic metal, i.e., silver is oxidized during the discharge reaction. The more noble metal is connected to the pole reduced during reaction.

Figure 1:
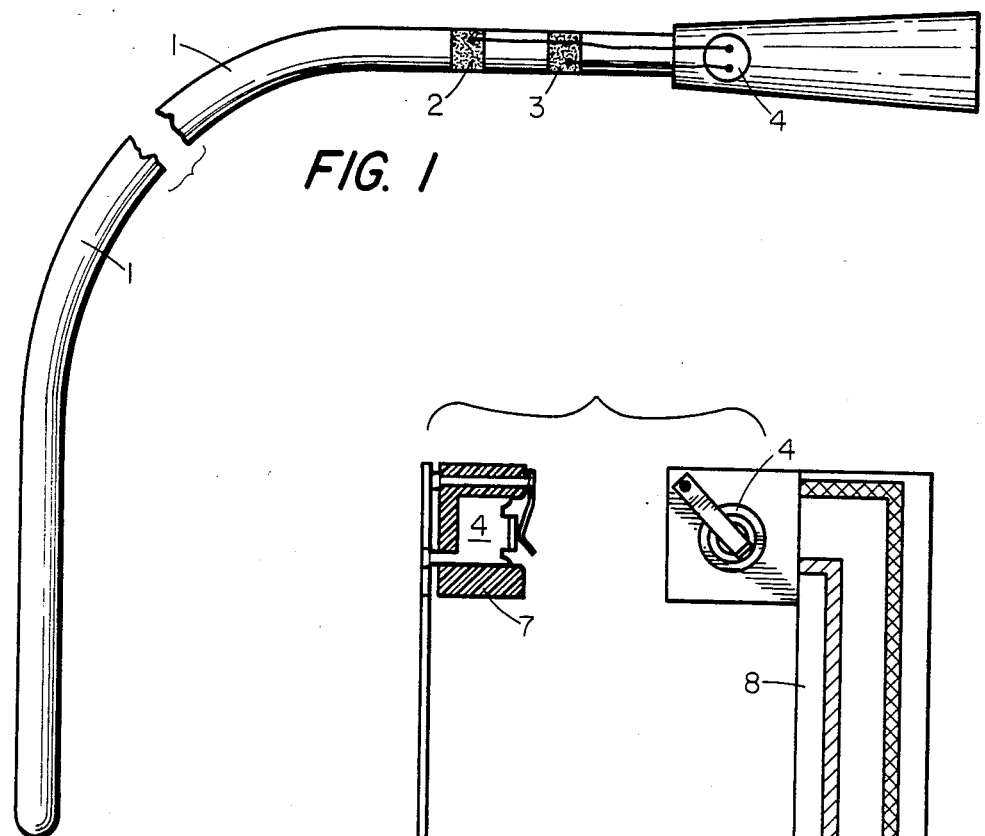
FIG. 1 is a catheter with bacterial barrier.

In the drawings, in FIG. 1 catheter 1 has attached or imbedded oligodynamic metal band 2 and separated therefrom parallel, more noble metal band 3. Bands 2 and 3 are connected to opposite poles of power cell 4, band 2 being connected to the oxidized pole (i.e. anode or positive pole). The bands are strategically positioned such that when the catheter is in place the bands are just within the body opening to the external environment.

Figure 2:
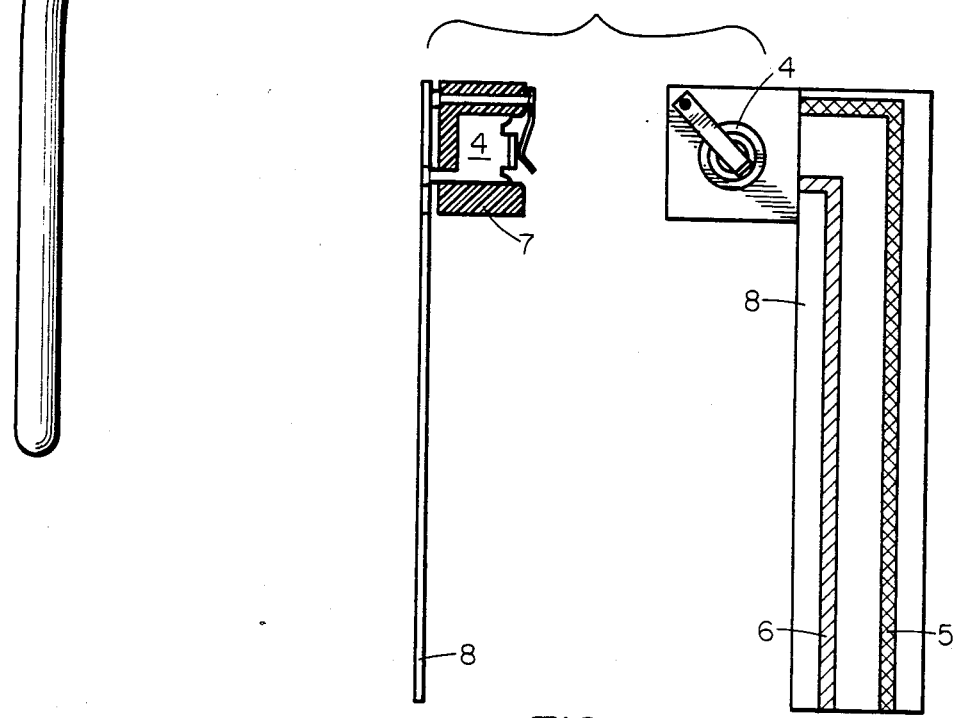
FIG. 2 is a bacterial barrier tape.

FIG. 2 depicts a front and side view of a flexible tape bacterial barrier comprising substrate 8, oligodynamic metal continuous strip 5 and more noble metal continuous strip 6 connected in open circuit to opposite poles of power cell 4 held in plastic holder 7. Continuous strips 5 and 6 correspond to bands 2 and 3 in FIG. 1 for wrapping around medical devices prior to insertion.

Figure 3:
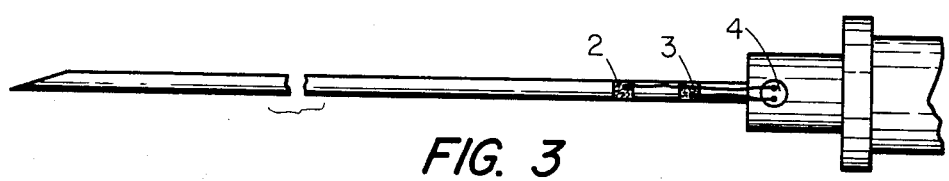
FIG. 3 is a vascular shunt with bacterial barrier.

FIG. 3 depicts a vascular shunt with bacterial barrier of oligodynamic metal band 2 and more noble metal band 3 connected to opposite poles of power cell 4.

While FIGS. 1 and 3 for clarity depict the power cell insulated connections to bands 2 and 3 as on the surface of the catheter or surgical shunt, in the preferred embodiment said connections would be imbedded in the substrate.

As an example of the invention, an oligodynamic metal strip of silver can be employed together with a more noble metal such as gold. Advantageously, silver can be used as an oligodynamic metal with the other being of substantially similar ionization potential such for this purpose copper or even stainless steel. While in certain half cell reactions copper is classified as less noble than silver, the ionization potentials of silver and copper differ by only 0.5 volt thus an electrochemical power cell (commonly 1.5 volt) can effectively electrolytically drive silver into ionization, i.e., oxidize silver, against the normal galvanic trend which would be to oxidize the copper.

Significantly, the tape according to this invention containing at least two strips of metal and a battery, has the battery in open circuit, thus the battery is assured of long storage life. Significant discharge would not begin until actual installation of the tape and intraluminal device into the patient. Conceivably, a solar cell can advantageously function as the electric power cell.

Since an electrochemical cell is used to oxidize the silver strip or band, the more noble metal in practice can be almost any conductive material including conductive plastic such as graphitized or carbonized plastics. Preferred however, is a more noble metal or a metal of substantially similar ionization potential as compared to the oligodynamic metal.

The body fluids and body mucosa serve as the electrolyte to complete the circuit by furnishing the ions for conductance between the positive and negative electrodes.

The power cell can be a battery or electrochemical cell and can be, for example, any of the common button batteries available today. A resistor would need to be included in the circuit to reduce the typical 1.5 V to the voltage levels needed. Microampere levels are sufficient current to achieve bactericidal effect. It is envisioned and preferred that as clinical acceptance is gained, that the battery be customized into a flat thinner and possibly flexible configuration especially since only microamperes current levels are required.

Where the tape or band is built into for example a catheter, the battery thickness can to some extent be incorporated into the wall thickness of the catheter itself.

The band or tape having at least two essentially parallel strips, bands or wires of silver and a less noble metal respectively, is positioned on the outside surface of a luminal or vascular device so as to occupy a position as just within a body opening to the external environment.

Where a detachable tape is used, the metal strip preferably should be exposed on both the top and underside of the tape. In the built-in versions where the tape is permanently adhered to a luminal or vascular device or where the metal bands are formed directly on the surface of the luminal or vascular device, only the side contacting the body tissues needs to be exposed.

The essentially parallel metal strips should consist of one strip of an oligodynamic metal such as silver, copper, or aluminum and a strip of a more noble metal such as platinum or gold separated from one another, more or less a distance of 1 cm. As can be discerned from reduction potential tables, with copper as the oligodynamic metal, the less noble metal can be silver. However copper has only about 5% the bactericidal effect of silver. Stainless steel can function as the more noble metal when, for example, connected to the reducing pole of the electrochemical cell. It is evident that multiple strips of one or both of the metals can be employed but are not believed essential and in the preferred embodiment single strips of each respective metal are employed.

The metal strips can be formed in thin flexible strips or bands or wires by any common technique such as metal sputtering or extrusion or other well known processes.

The preferred embodiment of a bacterial barrier for intraluminal and intravenal medical devices comprises a silver strip or band connected to the positive pole of an electrochemical cell and another metal strip or band such as copper or stainless steel connected to the negative pole such that silver is electrolytically driven into solution via ionization.

It is possible to advantageously employ the oligodynamic metal as a sacrificial galvanic anode thus eliminating necessity for a battery to drive the system. For example, where the silver strip is directly connected to a parallel gold strip, a bacterial barrier of silver ions would form by galvanic action because of the dissimilar reduction potentials of the respective metals.

In the case of silver and copper, silver has an apparent ionization potential of about 0.79 volts and copper about 0.34 volts. Where a silver strip is directly connected to a parallel copper strip typically a bacterial barrier of copper is expected to form. However, depending on the salts present either copper or silver can function as the less noble metal and be oxidized. Low pH values (acidic) favor copper ion formation, however, neutral to alkaline pH levels and the presence of chloride salts give rise to galvanic production of silver ions.

The tape with parallel metal strips and optional but preferred electrochemical cell when designed as a wrap around tape should have suitable fastening means such as adhesvie, Velcro ®, or can advantageously use electrostatic adhesion or stretched adhesion as is typical of many clear plastic wraps.

The intraluminal catheter, vascular device such as an intravenal surgical shunt or intraluminal device (medical device) with bacterial barrier according to this invention when inserted into the patient has the bacterial barrier positioned as just within the orifice or body opening, and the metal bands of the bacterial barrier are located on the outside surface of the medical device at the medical device/body wall interface. The body mucosa serves as electrolyte to complete the circuit. The less noble metal, preferably silver, ionizes giving rise to a strategically positioned bactericidal effect at the medical device/body wall interface which is considered the major pathway for infection.

The bacterial barrier of the present invention can also take the embodiment of an improved bandage having a circumferential strip of oligodynamic metal positioned around the circumference or primeter of the wound side of the bandage. The electrochemical cell's oxidizing pole is connected to the oligodynamic metal. The opposite pole is connected to the substantially parallel more noble metal or alternatively can be left as an uninsulated contact positioned on the inside of the bandage to contact the body wound fluids and thus complete the circuit.

It will be evident to those skilled in the art that, while specific embodiments have been illustrated and described, various modifications and changes may be made without departing from the spirit and scope of the invention. One obvious modification would be to place an electrolytic gel such as a hydrophilic gel containing an electrolytic salt such as sodium acetate, or a gel with protargin, or a gel of salts of normal body fluids between the band of oligodynamic metal and more noble conductor so as to help initiate an immediate bactericidal ion effect rather than relying solely on body electrolytic solutions for circuit completion. Other similar obvious modifications not departing from the scope of the invention are readily apparent.

I claim:

1. A bacterial barrier for medical devices comprising:
   a thin, flexible nonconductive substrate;
   an electric power cell;
   a continuous strip of an oligodynamic metal on the substrate;
   a conductive material on the substrate separated from the oligodynamic metal;
   the oligodynamic metal and conductive material being connected to oxidizing and reducing poles respectively of the electric power cell such that an open circuit is formed which circuit is closed by body fluids when the medical device with bacterial barrier is installed in a patient and such that the oligodynamic metal is oxidized forming ions of the oligodynamic metal.

2. The bacterial barrier according to claim 1 wherein said conductive material on the substrate is a continuous strip of conductive material substantially parallel to the strip of oligodynamic metal.

3. The bacterial barrier according to claim 1 wherein said oligodynamic metal is selected from silver, copper, aluminum or zinc.

4. The bacterial barrier according to claim 1 wherein said power cell is an electrochemical cell or solar cell.

5. The bacterial barrier according to claim 1 wherein said conductive material is a metal more noble than the oligodynamic metal or of substantially similar ionization potential.

6. The bacterial barrier according to claim 1 wherein the medical device is a catheter, the substrate is an outside wall of the catheter, and the bacterial barrier is positioned around the outside circumference of said catheter such that a continuous band of the oligodynamic metal is formed.

7. The bacterial barrier according to claim 6 wherein the bacterial barrier is positioned on the catheter to be just within the urethral orifice when the catheter is installed.

8. An improved medical device for shunting body fluids having a bacterial barrier around the outside circumference thereof comprising:
   a nonconductive substrate;
   at least one band of an oligodynamic metal on the substrate;
   an electric power cell;
   a conductive material on the substrate separated from the oligodynamic metal;
   the oligodynamic metal and conductive material being connected to oxidizing and reducing poles respectively of the electric power cell such that an open circuit is formed which circuit is closed by body fluids when the medical device with bacterial barrier is installed in a patient and such that the oligodynamic metal band is oxidized forming ions of the oligodynamic metal.

9. The device according to claim 8 wherein said conductive material is on the substrate and is a band substantially parallel to the band of oligodynamic metal.

10. The device according to claim 8 wherein the medical device is selected from the group consisting of a catheter, an intraveneous needle, and a vascular shunt.

11. The device according to claim 8 wherein said conductive material is a metal more noble than the oligodynamic metal or of substantially similar ionization potential.

12. The device according to claim 8 wherein said oligodynamic metal is selected from the group consisting of silver, copper, aluminum, and zinc.

13. The device according to claim 8 wherein said power cell is an electrochemical cell or solar cell.

14. The device according to claim 8 comprising in addition on electrolytic gel connecting the oligodynamic metal and the conductive metal.

15. The device according to claim 14 wherein said oligodynamic metal is selected from the group consisting of silver, copper, aluminum or zinc.

* * * * *

UNITED STATES PATENT AND TRADEMARK OFFICE
CERTIFICATE OF CORRECTION

PATENT NO. : 4,569,673
DATED : February 11, 1986
INVENTOR(S) : Julius M. Tesi

It is certified that error appears in the above-identified patent and that said Letters Patent is hereby corrected as shown below:

Column 6, line 64, "conductive metal" should read
-- conductive material --.

Signed and Sealed this

First Day of September, 1987

*Attest:*

DONALD J. QUIGG

*Attesting Officer*  *Commissioner of Patents and Trademarks*